US008551964B2

(12) United States Patent
Ross et al.

(10) Patent No.: US 8,551,964 B2
(45) Date of Patent: Oct. 8, 2013

(54) HSP90 INHIBITORS WITH MODIFIED TOXICITY

(75) Inventors: David Ross, Boulder, CO (US); David Siegel, Denver, CO (US); Wenchang Guo, Elk Grove, CA (US); Christopher J. Moody, Leeds (GB); Christopher S. P. McErlean, Eden's Landing (AU)

(73) Assignee: The Regents of the University of Colorado, Denver, CO (US)

( * ) Notice: Subject to any disclaimer, the term of this patent is extended or adjusted under 35 U.S.C. 154(b) by 282 days.

(21) Appl. No.: 12/673,996

(22) PCT Filed: Aug. 22, 2008

(86) PCT No.: PCT/US2008/074077
§ 371 (c)(1),
(2), (4) Date: May 24, 2011

(87) PCT Pub. No.: WO2009/026548
PCT Pub. Date: Feb. 26, 2009

(65) Prior Publication Data
US 2012/0022011 A1 Jan. 26, 2012

Related U.S. Application Data

(60) Provisional application No. 60/957,682, filed on Aug. 23, 2007.

(51) Int. Cl.
*A61K 31/704* (2006.01)
(52) U.S. Cl.
USPC .......................................................... 514/34
(58) Field of Classification Search
USPC .......................................................... 514/34
See application file for complete search history.

(56) References Cited

U.S. PATENT DOCUMENTS

| | | | |
|---|---|---|---|
| 2,601,994 | A | 7/1952 | Richman |
| 6,015,659 | A | 1/2000 | Welch et al. |
| 6,855,705 | B1 | 2/2005 | Tian et al. |
| 6,872,715 | B2 | 3/2005 | Santi et al. |
| 7,282,493 | B2 | 10/2007 | Adams et al. |
| 7,608,611 | B2 | 10/2009 | Ross et al. |
| 7,776,849 | B2 * | 8/2010 | Yamaguchi et al. .......... 514/183 |
| 2005/0054625 | A1 | 3/2005 | Johnson, Jr. et al. |
| 2006/0019941 | A1 | 1/2006 | Adams et al. |
| 2006/0205705 | A1 * | 9/2006 | Ross et al. .................... 514/183 |

FOREIGN PATENT DOCUMENTS

| | | |
|---|---|---|
| GB | 2042523 | 9/1980 |
| JP | 57-163369 | * 10/1982 |
| JP | 57163369 | * 10/1982 |
| WO | WO 94/08578 | 4/1994 |
| WO | WO 02/079167 | 10/2002 |
| WO | WO 03/066005 | 8/2003 |
| WO | WO 2005/063714 | 7/2005 |
| WO | WO 2005/095347 | 10/2005 |
| WO | WO 2006/098761 | 9/2006 |
| WO | WO 2007/001049 | 1/2007 |

OTHER PUBLICATIONS

Sporn MB and Harris ED. Proliferative diseases. Am J Med 70:1231-1236, 1981 (Jun. 1981).*
Andrus et al., "Total Synthese of (+)-Geldanamycin and (-)-o-Quinogeldanamycin: Asymmetric Clycolate Aldol Reactions and Biological Evaluation," Journal of Organic Chemistry, 2003, 68, pp. 8162-8169.
Ariese et al., "Comparison of Laurentian Fulvic Acid Luminescence with that of the Hydroquinone/quinone Model System: Evidence from low Temperature Fluorescence Studies and EPR Spectroscopy," Aquatic Sciences, 2004, 66, pp. 86-94.
Berge et al. Journal of Pharmaceutical Sciences, 1977, 66( 1), 1-19.
Cysyk et al., "Reaction of Geldanamycin and C17-Substituted Analogues with Gluthathione: Product Indentifications and Pharmacological Implications", Chem Res. Toxicol., 2006, vol. 19, pp. 376-381.
Dehn et al., "Development of a new isogenic cell-xenograft system for evaluation of NAD(P)H:quinone oxidoreductase-directed antitumor quinones: evaluation of the activity of RH1.", Clin. Cancer Res., May 1, 2004, vol. 10, No. 9, pp. 3147-3155.
Guo et al., "Formation of 17-Allylamino-demethoxygeldanamycin (17-AAG) hydroquinone by NAD (P) H:quinone oxidoreductase 1: role of 17-AAG hydroquinonein heat shock protein 90 inhibition", Cancer Res., Nov. 1, 2005, vol. 65, No. 21, pp. 10006-10015.
Guo et al., "The Bioreduction of a Series of Benzoquinone Ansamycins by NAD(P)H: Quinone Oxidoreductase 1 to more potent heat shock protein 90 inhibitors, the Hydroquinone Ansamycins", Molecular Pharmacology, 2006, vol. 70, No. 4, pp. 1194-1203.
Hu et al., "Isolation and characterization of novel geldanamycin analogs", Journal of Antibiotics, 2004, vol. 57, No. 7, pp. 421-428.
Kelland et al., "DT-Diaphorase expression and tumor cell sensitivity to 17-allylamino, 17-demethoxygeldanamycin, an inhibitor of heat shock protein 90", Journal of the National Cancer Institute, Nov. 17, 1999, vol. 91, No. 22, pp. 1940-1949.
Lucken, "Ion-Association and Specific Soluation in the Electron Spin Resonance Spectra of Semiquinones," The Journal of the Chemical Society, 1964, pp. 4234-4240.
Miller et al., "Depletion of the erbB-2 Gene Product p185 by Benzoquinoid Ansamycins," Cancer Research, 1994, pp. 2724-2730.
Ross, "Quinone Reductases Multiasking in the Metabolic World," Drug Metabolism Reviews, 2004, 36 (3-4), 659-654.
Schnur et al., "Inhibition of the Oncogene Product p185 in Vitro and in Vivo by Geldanamycin and Dihydrogeldanamycin Derivatives," Journal of Medicinal Chemistry, 1995, 38, p. 3806-3812.
Secretary, Codex Alimentarius Commission. Codex alimentarius commission, World Health Organization, CL 2002/7-NFSDU, Mar. 2002, 8 pages.

(Continued)

*Primary Examiner* — Wu-Cheng Winston Shen
*Assistant Examiner* — Yih-Horng Shiao
(74) *Attorney, Agent, or Firm* — Sheridan Ross P.C.

(57) ABSTRACT

The invention provides 19-substituted geldanamycin derivatives, pharmaceutically acceptable salts thereof and prodrugs thereof that are potent Hsp90 binding agents useful for the treatment of, and/or the amelioration of symptoms of, cancer and other proliferative tissue disorders.

9 Claims, 7 Drawing Sheets

(56) References Cited

OTHER PUBLICATIONS

Tadtong et al., "Geldanamycin derivatives and neuroprotecetive effect on cultured P19-derived neurons," Bioorganic & Medicinal Chemistry Letters, vol. 17, No. 10, Apr. 27, 2007, pp. 2939-2943.

Tziveleka et al., "Antioxidant Potential of Natural and Synthesised Polyprenylated Hydorquinones", Bioorganic and Medical Chemistry, 2002, vol. 10, pp. 935-939.

Whitesell et al. "Inhibition of Heat Shock Protein HSP90-pp60 Heteroprotein Complex Formation by Benzoquinone Ansamycins: Essential Role for Stress Proteins in Oncogenic Transformation," Proceedings of the National Academy of Sciences, 1994, vol. 91, 8324-8328.

International Search Report for International (PCT) Patent Application No. PCT/US05/31524, mailed May 17, 2007.

Written Opinion for International (PCT) Patent Application No. PCT/US05/31524, mailed May 17, 2007.

International Preliminary Report on Patentability for International (PCT) Patent Application No. PCT/US2005/031524, mailed Sep. 20, 2007.

Extended European Search Report or Application No. EP 05810418.3, dated Feb. 16, 2009.

Communication from European Patent Office for European Patent Application No. 05810418.3, dated Feb. 11, 2010.

Official Action for European Patent Application No. 05810418.3, dated Apr. 14, 2011 4 pages.

International Search Report for International (PCT) Patent Application No. PCT/US08/74077, mailed Nov. 19, 2008.

Written Opinion for International (PCT) Patent Application No. PCT/US08/74077, mailed Nov. 19, 2008.

International Preliminary Report on Patentability for International (PCT) Patent Application No. PCT/US2008/074077, mailed Mar. 4, 2010.

Search Report for European Patent Application No. 08798530.5, dated Mar. 22, 2011.

Official Action for U.S. Appl. No. 11/218,320, mailed Jul. 10, 2007.
Official Action for U.S. Appl. No. 11/218,320, mailed Apr. 17, 2008.
Official Action for U.S. Appl. No. 11/218,320, mailed Sep. 15, 2008.
Notice of Allowance for U.S. Appl. No. 11/218,320, mailed Jun. 25, 2009.

* cited by examiner

HSP90 INHIBITORS WITH MODIFIED TOXICITY

CROSS REFERENCE TO RELATED APPLICATION

This application is a national stage application under 35 U.S.C. 371 of PCT Application No. PCT/US2008/074077 having an international filing date of Aug. 22, 2008, which designated the United States, which PCT application claimed the benefit of U.S. Provisional Application No. 60/957,682, filed Aug. 23, 2007. The entire disclosure of each of these priority documents are hereby incorporated by reference.

GOVERNMENT INTEREST

This invention was made with government support under grant number CA051210 awarded by the National Institutes of Health. The government has certain rights in the invention.

FIELD OF INVENTION

This invention relates to geldanamycin derivatives as anti-cancer compounds, pharmaceutical compositions containing the same, and methods of using the same in the treatment of neoplastic disorders and solid tumors in a mammal.

BACKGROUND OF INVENTION

Hsp90 is a protein chaperone that utilizes the hydrolysis of ATP to assist in the folding of early nascent forms of proteins to their mature, correctly-folded forms. Once the protein has been correctly folded, Hsp90 is released and thus, it functions as a true protein "catalyst." Hsp90 has also been recognized as an attractive anticancer target in that this chaperone assists in the folding of many oncogenic proteins including ErbB2, Raf-1, mutant p53, estrogen and steroid receptors. Thus, by inhibiting Hsp90, a large number of downstream oncogenic proteins can be disrupted, thereby attacking the neoplastic process at a number of points.

The first Hsp90 inhibitor used clinically was geldanamycin. Geldanamycin is a benzoquinone ansamycin polyketide isolated from *Streptomyces geldanus*. Although originally discovered by screening microbial extracts for antibacterial and antiviral activity, geldanamycin was later found to be cytotoxic to tumor cells in vitro and to reverse the neoplastic morphology of cells transformed by the Rous sarcoma virus.

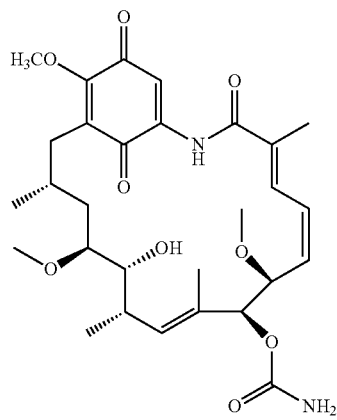

Geldanamycin

Unfortunately, the administration of geldanamycin produced unacceptable hepatotoxicity, which led to its withdrawal from Phase I clinical trials. The toxicity of these compounds is believed to be a result, at least in part, of glutathione depletion. Second generation geldanamycin derivatives were developed including 17-demethoxy-17-(2-propenylamino)-geldanamycin (17AAG; also known as 17-allylaminogeldanamycin) and 17-demethoxy-17-[[2-(dimethylamino)ethyl]amino]-geldanamycin (17-DMAG). These molecules reduce liver toxicity and have shown success in Phase I and Phase II clinical trials.

While there has been a great deal of research interest in the benzoquinone ansamycins, particularly geldanamycin and 17-AAG, there remains a need for effective derivatives of these compounds having higher activity without the significant risk of toxicity of the parent geldanamycin compound.

SUMMARY OF INVENTION

The present invention provides novel geldanamycin derivatives (quinone and hydroquinone ansamycins) modified at the 19 position of the geldanamycin molecule, and pharmaceutically acceptable salts thereof and prodrugs thereof that are potent Hsp90 binding agents with improved toxicity profiles relative to the parent quinones and hydroquinones. The 19-substituted benzoquinone and hydroquinone ansamycins of the present invention do not deplete glutathione and are therefore less hepatotoxic.

The present invention also provides methods of making and using these novel compounds as well as pharmaceutical compositions containing these compounds.

One embodiment of the invention is a purified compound having the chemical structure of Formula I:

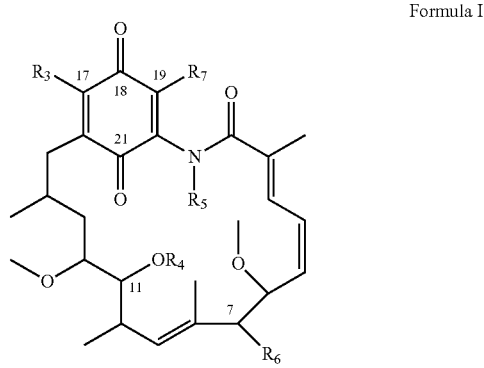

Formula I or a pharmaceutically-acceptable salt thereof;
wherein:
$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; wherein when $R_7$ is Br, $R_3$ is not $OCH_3$;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is OH, $NH_2$, CN, halogen, $C_1$-$C_4$ alkyl, $C_1$-$C_6$ cycloalkyl, alkoxy, alkylhalide, or alkylthiol.

A preferred embodiment, is a purified compound having the chemical structure of Formula I, wherein:

$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are H, $R_6$ is $OC(=O)NH_2$, and, $R_7$ is F, Cl, $CH_3$, $CF_3$ or alkoxy.

Another embodiment of the invention is a purified compound having the chemical structure of Formula II:

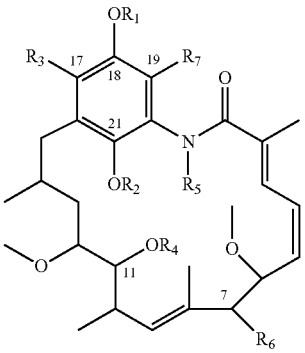

Formula II or a pharmaceutically-acceptable salt thereof;
wherein:

$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$, wherein X=an amino acid side chain;

$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]allyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; wherein when $R_7$ is Br, $R_3$ is not $OCH_3$;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is OH, $NH_2$, halogen, $C_1$-$C_4$ alkyl, $C_1$-$C_6$ cycloalkyl, alkoxy, alkylhalide, or alkylthiol.

A preferred embodiment of the invention is a purified compound having the chemical structure of Formula II, wherein:

$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are H, $R_6$ is $OC(=O)NH_2$, and, $R_7$ is F, Cl, $CH_3$, $CF_3$ or alkoxy.

One embodiment of this invention is a method of treating cancer or other proliferative diseases, or ameliorating the symptoms of these diseases, by administering a therapeutically effective amount of one of these compounds, or a pharmaceutically acceptable salt form thereof, or prodrugs thereof to a mammal in need of such treatment or suspected of having a cancer or other proliferative disease.

Another embodiment of this invention is a method of treating cancer or other proliferative diseases, or ameliorating a symptom thereof, by administering a therapeutically effective combination of one of the compounds of the present invention and one or more other known anti-cancer or anti-proliferative compounds. For example, the other anti-cancer compounds include at least one of a tyrosine kinase inhibitor, paclitaxel and doxorubicin.

Another embodiment of this invention is a method of treating cancer or other proliferative diseases, or ameliorating a symptom thereof, by administering a therapeutically effective amount of one of the compounds of the present invention in conjunction with medically supervised radiation therapy.

Another embodiment of the present invention is a method of inhibiting the Hsp90 activity in a cell by contacting the cell with one or more of the compounds of the present invention.

Another embodiment of the present invention is a method of disrupting the folding of a protein such as, but not limited to, ErbB2, Raf-1, mutant p53, estrogen and steroid receptors in a cell by contacting the cell with one or more of the compounds of the present invention.

Another embodiment of the present invention is a method of increasing Hsp70 expression in a cell by contacting the cell with one or more of the compounds of the present invention. This method may be used to treat a neurodegenerative disease in a mammal by the administration of one or more of the compounds of the present invention to the mammal resulting in the increased expression of Hsp70, which may have the effect of inhibiting or ameliorating the symptoms of a neurodegenerative disease.

Another embodiment of the present invention is a method of increasing Raf-1 degradation in a cell by contacting the cell with one or more of the compounds of the present invention. Another embodiment of the present invention is a method of decreasing MEK and/or ERK phosphorylation in a cell by contacting the cell with one or more of the compounds of the present invention.

Another embodiment of this invention is a method of testing the susceptibility of a mammal to treatment with one of the compounds of the present invention by testing the mammal for the presence of a mutation in the NQO1 gene in the mammal wherein the presence of a mutation in the NQO1 gene is indicative of limited, or no susceptibility to response to a compound of the present invention by the mammal.

Another embodiment of this invention is a method of testing the susceptibility of a mammal to treatment with one of the compounds of the present invention by testing the mammal for the presence NQO1 enzymatic activity in the mammal, wherein reduced or absent NQO1 enzymatic activity is indicative of limited or no susceptibility to response to a compound of the present invention by the mammal.

Additional embodiments of the present invention include the use of metal chelating agents to prevent or reduce the autoxidation of the hydroquinone ansamycin derivatives of the present invention to the corresponding quinione compounds during storage or administration. Additionally, the invention provides pharmaceutical compositions containing hydroquinone ansamycin derivatives and a metal chelating agent.

DESCRIPTION OF EMBODIMENTS

Figure 1:
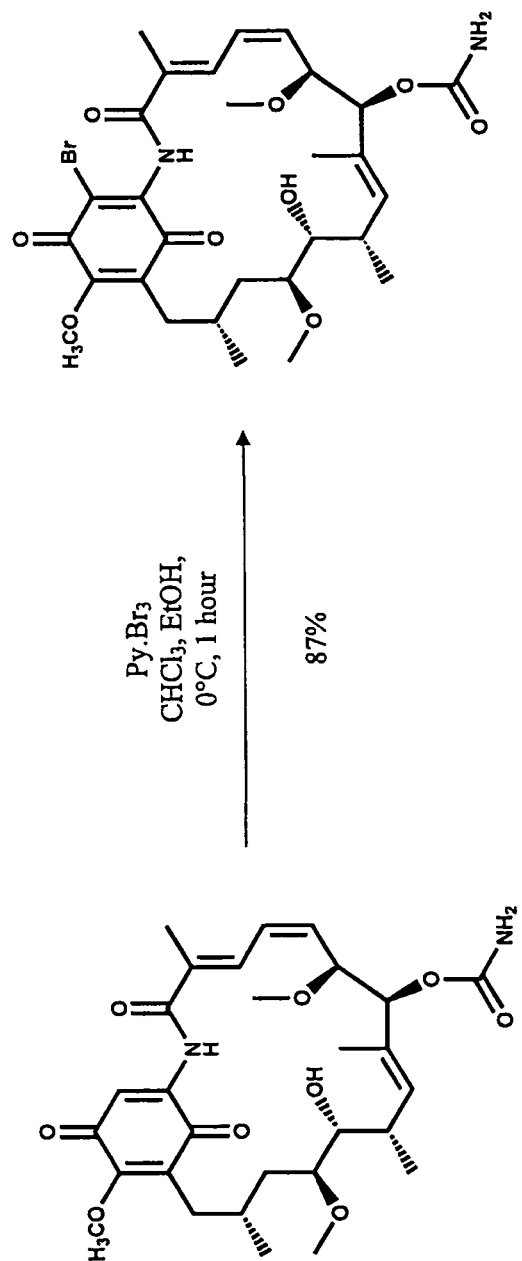
FIG. 1 shows the synthetic scheme for the synthesis of the compounds of the present invention.

The present invention is drawn to methods of treating cancer or other proliferative diseases in a mammal by the administration of a therapeutically-effective amount of novel 19-substituted geldanamycin derivatives, pharmaceutically-acceptable salts and/or prodrugs thereof to the mammal. These 19-substituted geldanamycin derivatives produce significantly less hepatotoxicity than geldanamycin as they do not deplete glutathione. Additionally, the invention provides novel 19-substituted geldanamycin derivatives, pharmaceutically-acceptable salts and/or prodrugs thereof for use in pharmaceutical compositions to be administered to a mammal.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., Hawley's Condensed Chemical Dictionary (13 ed.), R. J. Lewis, ed., J. Wiley & Sons, Inc., New York (1997)). Aryl groups include, without limitation, phenyl, naphthyl, indanyl and indenyl.

"Alkenyl" as used herein by itself or as part of another group refers to straight or branched chain substituent of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted in the same manner as that described for alkyl groups.

The term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, which may be substituted, in the same manner as that described for alkyl groups.

"Alkoxy" means —OR where R is alkyl as defined above, e.g., methoxy, ethoxy, propoxy, 2-propoxy, acetyl and the like.

"Alkylthiol" means —SR where R is alkyl, as defined above.

"Alkylhalide" designates an alkyl group, as defined above, substituted with one or more halides (F, Cl, Br, I).

"Alkynyl" means a linear monovalent hydrocarbon of two to six carbon atoms or a branched divalent hydrocarbon of three to six carbon atoms, containing at least one triple bond, e.g., ethynyl, propynyl, and the like.

The term "halogen" refers to nonmetal elements from Group 17 of the periodic table, including fluorine, F; chlorine, Cl; bromine, Br; iodine, I; and astatine, At.

The term "amino acid side chain" refers to the side chain of any of the known alpha-amino acids such as the side chain of arginine, histidine, alanine, glycine, lysine, glutamine, leucine, valine, serine, homoserine, allothreonine, naphthylalanine, isoleucine, phenylalanine and the like. In instances in which a compound is synthesized or derivatized to include an amino acid side chain, the side chain used is preferably chosen from the side chains of the naturally-occurring amino acids.

The term "glycoside" refers to any compound that contains a carbohydrate molecule (sugar), bonded through its anomeric carbon to a non-sugar group by either an oxygen or a nitrogen atom.

The term "glucuronide" as used herein refers to the compound or metabolite that results from the reaction of glucuronic acid with an acid or alcohol or phenol moiety on the parent compound to form a covalent link between the parent compound and the glucuronic acid through a glycosidic bond.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is replaced with a selection from the indicated group, provided that the designated atom's normal valency is not exceeded, and that the substitution results in a stable compound.

"Unsubstituted" atoms bear all of the hydrogen atoms dictated by their valency. When a substituent is keto, then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418.

"Prodrugs" are intended to include any covalently bonded carriers that release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein an acyl, hydroxy, amino, or sulfhydryl group is bonded to any group that, when the prodrug of the present invention is administered to a mammalian subject, is cleaved to form a free acetyl, hydroxyl, free amino, or free sulfydryl group, respectively. Examples of prodrugs include, but are not limited to, acetate, formate, and benzoate derivatives of alcohol and amine functional groups in the compounds of the present invention.

The term "therapeutically-effective amount" of a compound of this invention means an amount effective to antagonize abnormal level of CRF or treat the symptoms of affective disorder, anxiety or depression in a host.

As used herein, the term "anti-cancer" or "anti-proliferative" agent includes, but is not limited to, tyrosine kinase inhibitors, paclitaxel and doxorubicin.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

Because the benzoquinone ansamycins contain a quinone moiety, bioreduction of these compounds to form semiquinone and hydroquinone species is a possible metabolic pathway in tumor cells in the presence of the appropriate bioreductive enzymes. The present inventors have previously demonstrated that the active forms of these benzoquinone ansamycins are the reduced forms, the hydroquinone ansamycins (Guo, W., Reigan, P., Siegel, D., Zirrolli, J., Gustafson, D., Ross, D. *Formation of 17-Allylamino-Demethoxygeldanamycin (17-AAG) Hydroquinone by NAD(P)H: Quinone Oxidoreductase 1: Role of 17-AAG Hydroquinone in Heat Shock Protein 90 Inhibition.* Cancer Res., 65(21):10006-15 (2005); Guo, W., Reigan, P., Siegel, D., Zirrolli, J., Gustafson, D., Ross, D. *The Bioreduction of a Series of Benzoquinone Ansamycins by NAD(P)H: Quinone Oxidoreductase 1 to More Potent Heat Shock Protein 90 Inhibitors, the Hydroquinone Ansamycins*, Mol. Pharmacol., 70(4):1194-1203 (2006)).

NQO1 (DT-diaphorase, EC 1.6.99.2) is a flavoenzyme capable of utilizing either NADH or NADPH as reducing cofactors to catalyze the direct two-electron reduction of quinones to hydroquinones. Thus, amongst the bioreductive enzymes expressed in cancer cells, NQO1 is poised to have the greatest influence on the metabolism and activation of the benzoquinone ansamycins to hydroquinones. NQO1 is expressed at high levels in many human cancers including lung, colon, stomach, pancreatic and breast cancers and has been shown to increase the cytotoxicity of many quinone containing antitumor drugs such as AZQ, mitomycin C, E09, streptonigrin, RH-1 and β-lapachone by reduction of these compounds to the corresponding hydroquinone species.

As noted above, the use of benzoquinone ansamycins has been limited by hepatotoxicity. Without intending to be bound by any one theory, it is believed that the hepatotoxicity may be a result of depletion of hepatic glutathione resulting from the participation of the benzoquinone ansamycins in both redox cycling and adduction reactions. Benzoquinone ansamycins can form glutathione adducts on the 19 position of the molecule the present inventors have isolated geldanamycin and 17-DMAG-glutathione adducts after reaction of 17-AAG with reduced glutathione. The present inventors have also shown that the benzoquinone ansamycins can redox cycle to generate reactive oxygen species, which also deplete glutathione. A reduction or elimination of the hepatotoxicity associated with these benzoquinone ansamycins, in either the quinone or hydroquinone forms, is believed to result from diminished hepatic glutathione depletion.

The compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods of synthesizing the 19-methyl substituted geldanamycin fall into two general categories. The first is a conjugate addition-elimination strategy, and the second is a palladium mediated sp2-sp3 cross coupling strategy. Both approaches start with the 19-bromo geldanamycin, which is commercially available, and utilize methyl organometallics (e.g., MeMgBr) that introduce the methyl group at the C-19 site. Details of these preferred synthesis methods are provided in Example 2 of this disclosure.

The compounds of this invention may be prepared using the reactions performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions will be readily apparent to one skilled in the art and alternate methods must then be used.

The benzoquinone ansamycin starting compound is available commercially from Invivogen. Preparation of 18,21-dixydroxy-geldanamycin derivatives is described in detail in co-pending U.S. patent application Ser. No. 11/218,320 (U.S. Patent Publication No. 2006-0205705 A1), which is incorporated herein, in its entirety, by reference.

Therefore, one embodiment of the present invention is a method of forming a 19-substituted benzoquinone ansamycin or a derivative thereof by treating a benzoquinone ansamycin or derivative as described in Example 1 and shown in FIG. 1. Another embodiment is a method of forming a 19-substituted benzoquinone or dihydroquinone ansamycin, or a derivative thereof, by treating a benzoquinone ansamycin or derivative as described in Example 2 and shown in FIGS. 2 and 3.

Also provided herein are pharmaceutical compositions containing compounds of this invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

The hydroquinone ansamycin derivatives of the present invention are relatively stable, undergoing autoxidation to the corresponding quinone compound over time. This autoxidation occurs more rapidly in the presence of metal salts, and particularly in the presence of copper. Therefore, metal chelating agents can be used to prevent the autoxidation of the hydroquinone derivatives of the present invention. Thus, one embodiment of the present invention is a method of reducing the autoxidation of a hydroquinone ansamycin derivative by storing the hydroquinone ansamycin derivative in the presence of a metal chelating agent. A related embodiment is a method of reducing the autoxidation of a hydroquinone ansamycin derivative by administering a therapeutically effective amount of a hydroquinone ansamycin derivative to a mammal in the presence of a metal chelating agent. A further embodiment of the invention is a pharmaceutical composition containing at least one of the ansamycin derivatives of the present invention and a metal chelating agent.

Unfortunately, some metal chelating agents or sequestrating agents may interfere with the Hsp90 inhibitory activity of a hydroquinone ansamycin or may cause adverse effects of their own. Therefore, preferred metal chelating agents and sequestrating agents of the present invention do not interfere with the activity of a hydroquinone ansamycin and do not produce toxic or other adverse events in an animal.

The metal chelating agent may be any compound that will bind metal ions without eliminating the activity of an ansamycin hydroquinone present in a composition containing the metal chelating agent. The addition of a protein metal chelating agent may minimize formulation problems encountered with hydroquinone drugs that result from formation of the corresponding quinone by autoxidation of the hydroquinone.

Exemplary metal chelating agents suitable for use in the methods and compositions of the present invention are proteins, hereinafter referred to as "protein metal chelating agents." Preferably, these protein metal chelating agents contain the ACTUN protein motif. This protein motif was characterized by Harford, et al (Acc. Chem. Res 30:123) in 1997, and is characterized by a free amino-terminus, a histidine residue in 3rd position and two intervening peptide nitrogens. A particularly preferred protein metal chelating agent containing the ACTUN protein motif that is useful in the methods and compositions of the present invention is albumin and more preferably, human albumin. Therefore, a preferred embodiment of the present invention is a composition containing an ansamycin hydroquinone and a protein metal chelating agent having an ACTUN motif. A preferred embodiment is a composition containing an ansamycin hydroquinone and albumin and more preferably, a composition containing an ansamycin hydroquinone and human albumin.

This invention further provides a method of treating a mammal afflicted with a cancer or proliferative disorder, which includes administering to the mammal a pharmaceutical composition provided herein. Such compositions generally comprise a therapeutically effective amount of a compound provided herein, that is, an amount effective to ameliorate, lessen, inhibit or destroy neoplastic tissue. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Additional objects, advantages, and novel features of this invention will become apparent to those skilled in the art upon examination of the following examples thereof, which are not intended to be limiting.

EXAMPLES

Example 1

Formation of a 19-Substituted Geldanamycin

19-Bromo geldanamycin analogues were readily synthesized from commercially available geldanamycin by electrophilic bromination with pyridium perbromide as shown in FIG. 1.

Example 2

Formation of a 19-Substituted Geldanamycin

Figure 2:
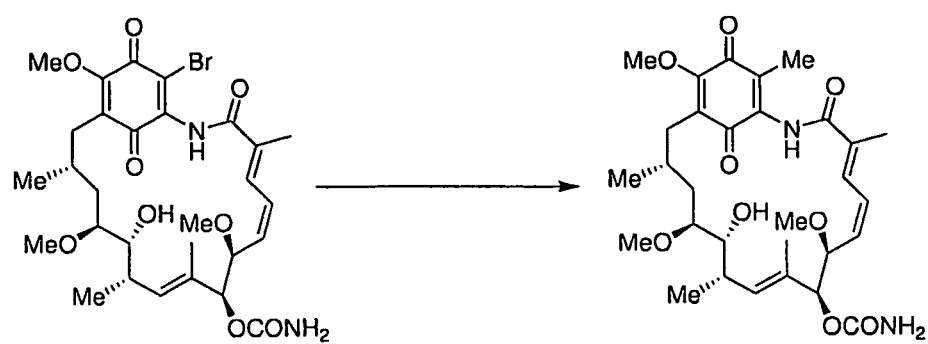
FIG. 2 shows a synthetic conversion of the 19-bromo geldanamycin to the 19-methyl geldanamycin compound of the present invention.
Figure 3:
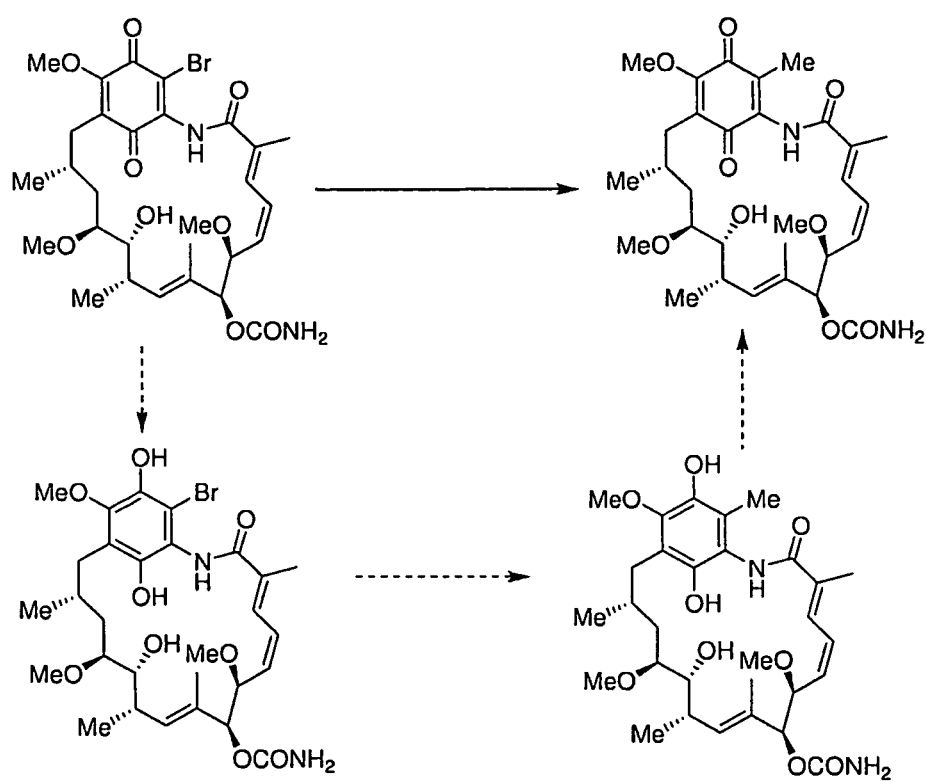
FIG. 3 shows a synthetic conversion of 19-bromo geldanamycin to 19-methyl geldanamycin and its dihydroquinone ansamycin derivative. The schemes of FIGS. 1-3 show the use of a geldanamycin starting material as an example, but one of skill in the art will readily recognize that these synthetic schemes are not limited to the geldanamycin molecule and may be generally applied to the use of benzoquinone ansamycin starting materials.
Figure 4A:
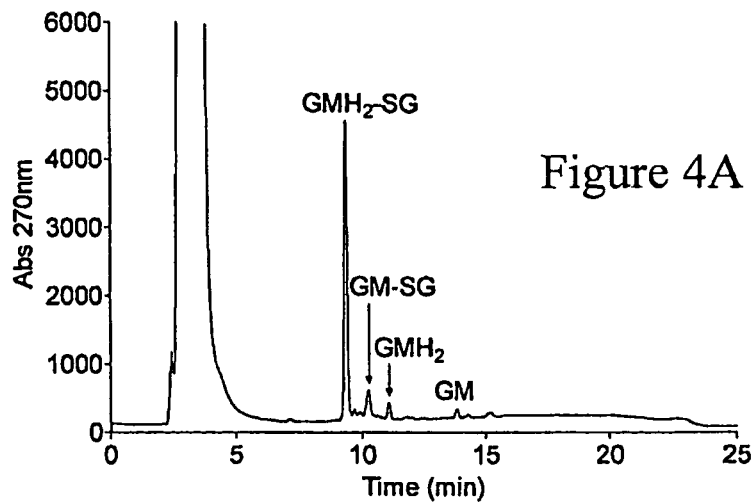
FIG. 4 shows HPLC and LC-MS analysis of the formation of GM-glutathione conjugates. GM-glutathione conjugate formation was analyzed by HPLC and LC-MS. Briefly, 50 µM GM, 500 µM NADH, and 5 mM glutathione in the absence and presence of 11.8 µg rh-NQO1 and in the absence or presence of 2 µM ES936, were incubated in 50 mM potassium phosphate buffer, pH 7.4 (1 ml) at room temperature for 5 min. GM-glutathione conjugate formation was analyzed by HPLC at 270 nm (5 min). A, GM and glutathione; B, GM, NADH, rhNQO1, and glutathione; C, GM, NADH, rhNQO1, ES936, and glutathione; D, LC-MS confirmed GMH2-SG and GM-SG as the product of the interaction of GM and glutathione.
Figure 4B:
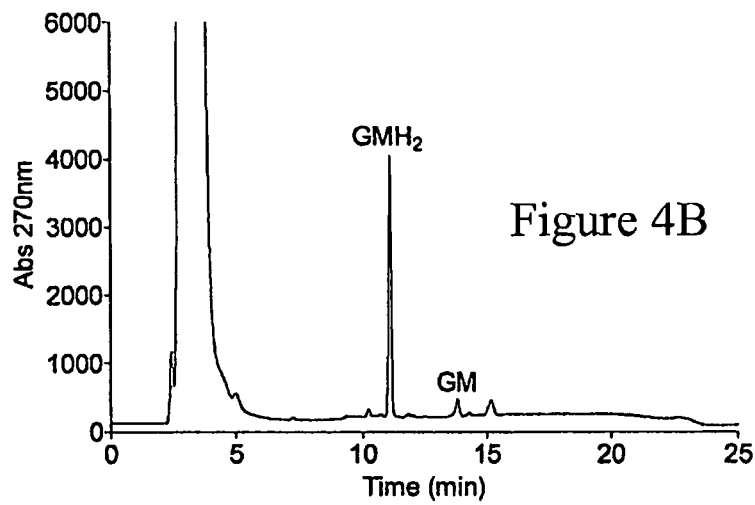
Figure 4C:
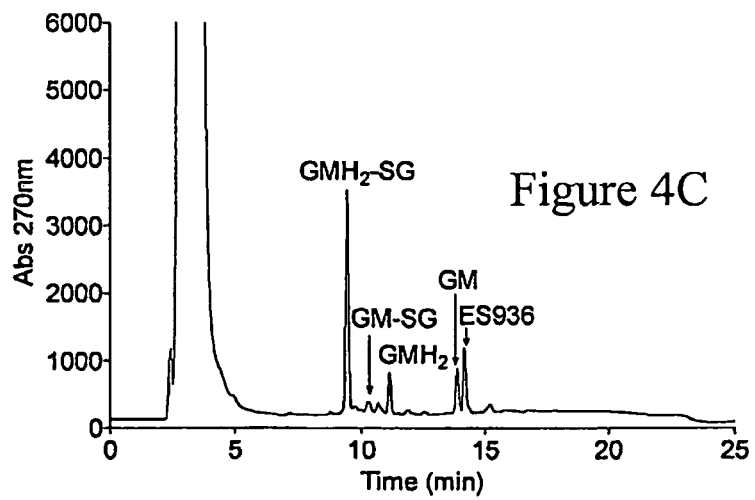
Figure 4D:
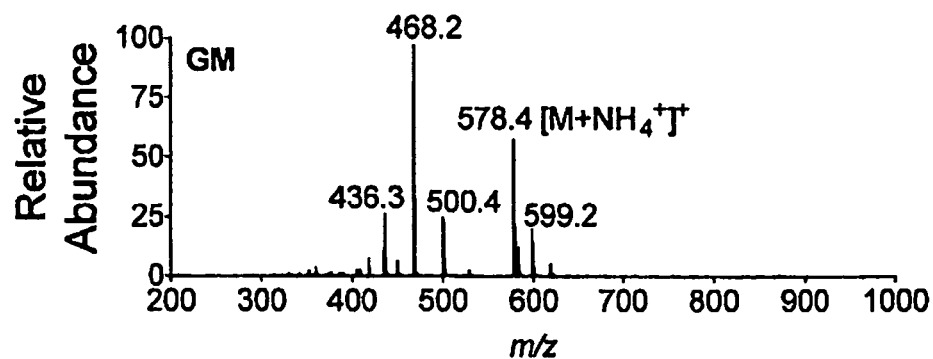
Figure 4D:
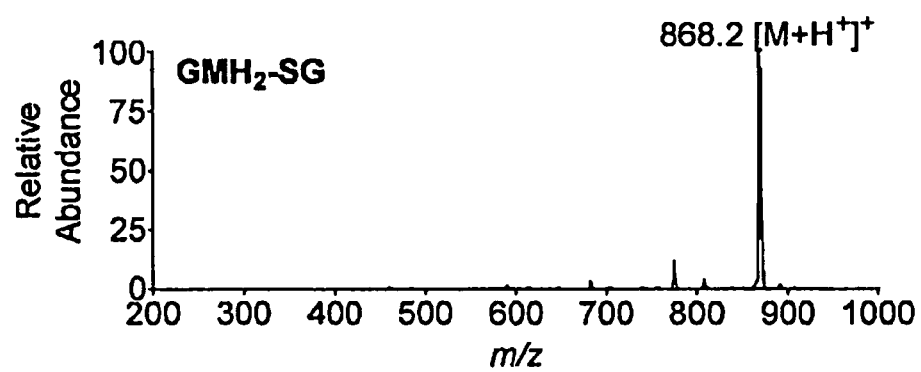
Figure 4D:
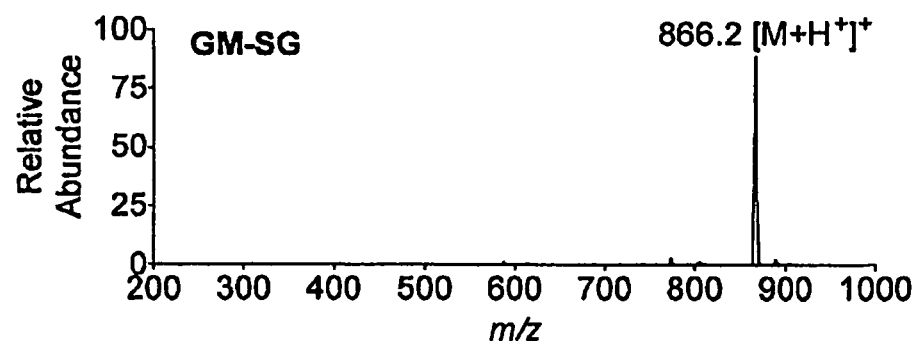
Figure 5A:
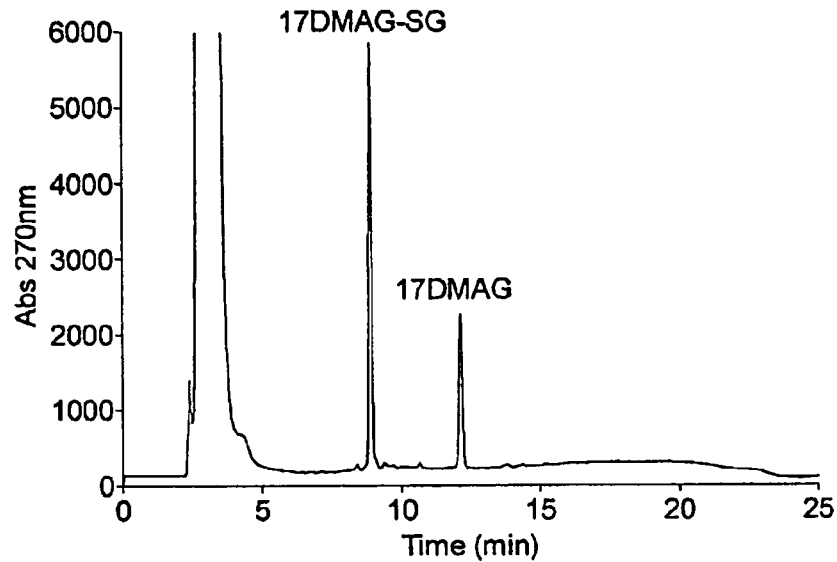
FIG. 5 shows HPLC and LC-MS analysis of the formation of 17DMAG-glutathione conjugates. Reaction conditions were: 50 µM 17DMAG, 500 µM NADH, and 5 mM glutathione, in the absence and presence of 11.8 µg rhNQO1 and in the absence or presence of 2 µM ES936, were incubated in 50 mM potassium phosphate buffer, pH 7.4 (1 ml) at room temperature for 3 h. 17DMAG-glutathione conjugate formation was analyzed by HPLC at 270 nm (3 h). A, 17DMAG and glutathione; B, 17DMAG, NADH, rhNQO1, and glutathione; C, 17DMAG, NADH, rhNQO1, ES936, and glutathione; D, LC-MS confirmed 17DMAG-SG as the product of the interaction of 17DMAG and glutathione.
Figure 5B:
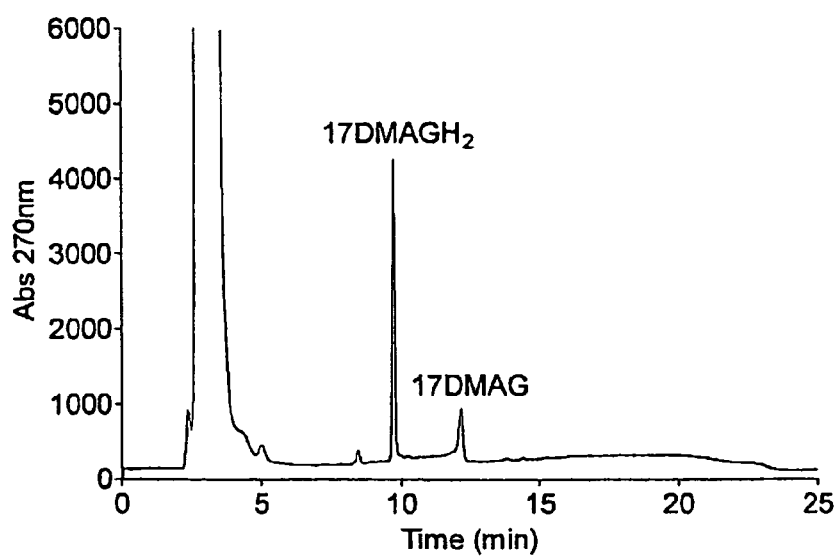
Figure 5C:
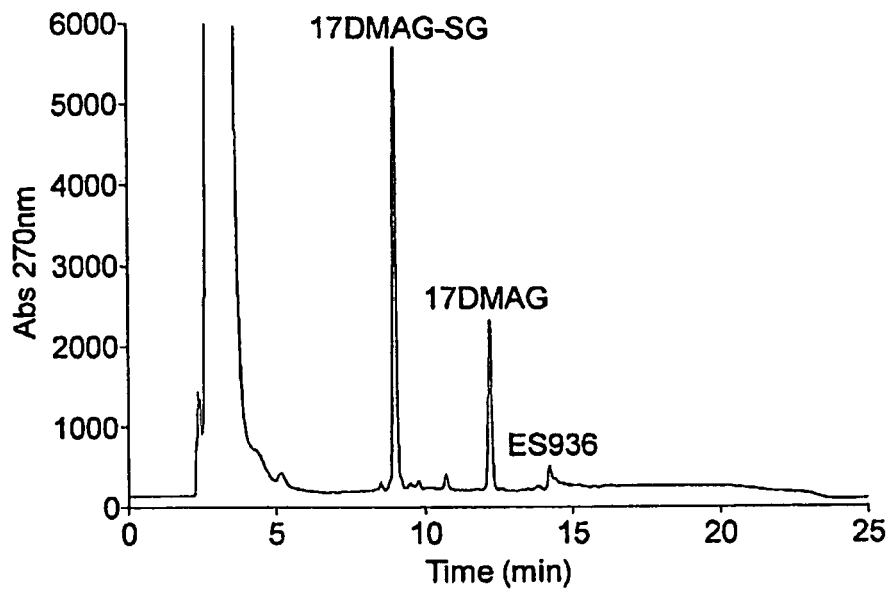
Figure 5D:
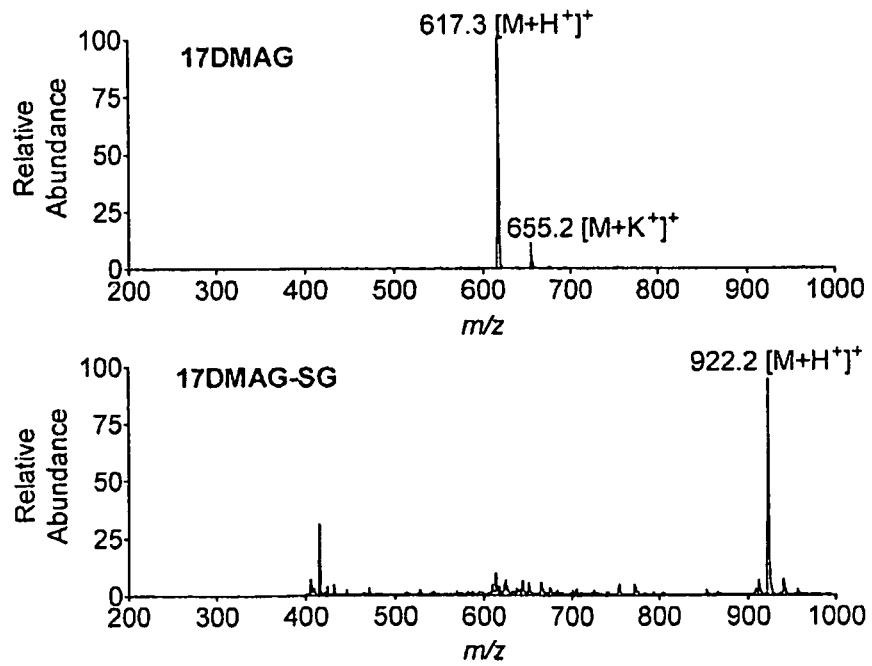

Two synthetic approaches can be utilized for the synthesis of 19-methyl substituted geldanamycin derivatives: a conjugate addition-elimination strategy, and a palladium mediated sp2-sp3 cross coupling strategy. Referring to FIGS. 2 and 3, both approaches start with the readily available 19-BrGA.

The addition-elimination procedure requires an organometallic species that will selectively attack at the C-19 site in preference to the C-1, C-3, C-5, C-16, C-17, C-18, C-20, C-21 or the carbamic acid residue. The reagents MeMgBr, MeLi in the presence of CuCl, and Fe(acac)$_3$ in the presence of MeMgBr, can be utilized in tetrahydrofuran (THF) solvent at 0° C.

The sp2-sp3 cross coupling strategy utilizes the Pd(Ph$_3$)$_4$ reagent in the presence of either CuCl and Me$_4$Sn, or in the presence of trimethylboroxine and K$_2$CO$_3$, in 1,4-dioxane solvent at 100° C. This approach has the added advantage that the quinone could also be reduced to the dihydroquinone to give aromatic bromides, which are well known to participate in palladium mediated methylations, shown in FIG. 3. The dihydroquinone could be reoxidised to the quinone or functionalised on the oxygen atoms, as shown in FIG. 3.

Example 3

Toxicity of Benzoquinone Ansamycins

Benzoquinone ansamycins (BAs) can be metabolized by one-electron reductases that interact with glutathione, and these reactions have been associated with hepatotoxicity. Using a series of BAs, the ability of BAs to be metabolized by one-electron reductases, and their conjugation with glutathione, was investigated. The BAs used were: geldanamycin (GM), 17-(allylamino)-17-demethoxygeldanamycin (17AAG), 17-demthoxy-17-[[2-(dimethylamino)ethyl]amino]-geldanamycin (17DMAG), 17-(amino)-17-demethoxygeldanamycin (17AG), and 17-demethoxy-17-[[2-(pyrrolidin-1-yl)ethyl]amino]-geldanamycin.

Analysis of NADPH-Cytochrome P450 Reductase-Mediated One-Electron Redox Cycling of BAs.

Using human and mouse liver microsomes and either NADPH or NADH as cofactors, the relative one-electron redox cycling rates of BAs mediated by NADPH-cytochrome P450 reductase were determined by measuring the rates of oxygen consumption. The rates of oxygen consumption and NAD(P)H oxidation were measured as indicators of the relative redox cycling rates of BAs. Reaction conditions were: 50 µM BA, 500 µM NADPH, and 3.3 µg of NADPH-cytochrome P450 reductase were incubated in 50 mM potassium phosphate buffer, pH 7.4 (3 ml) at 35° C. The oxygen consumption rate was measured using a Clark electrode (air tight) over 10 min. The results show that in this series of BAs, 17AAG was metabolized at the slowest rate, whereas GM was metabolized at a relatively rapid rate during either NADPH- or NADH-dependent metabolism in human and mouse liver microsomes.

Quinone/Hydroquinone Cycling in Microsomal Incubations.

The concentration of benzoquinone ansamycins and hydroquinone ansamycins formed in microsomal incubations was determined using HPLC. For GM and 17AAG, the concentration of GMH2 and 17AAGH2 in microsomal incubations was also determined using standard curves generated by HPLC. Briefly, mixtures containing 50 µM GM or 17AAG, 500 µM NADH, and 3.3 µg rhNQO1 were incubated in 50 mM potassium phosphate buffer, pH 7.4 (1 ml). The reactions were stopped with an equal volume of ice-cold methanol at 0, 0.5, 1, 2, and 5 min for GM or 0, 1, 5, 10, and 30 min for 17AAG and analyzed using HPLC. The amount of quinone remaining at the various time points was determined using standard curves. The amount of hydroquinone formed at the various time points was obtained by subtraction from the starting concentration of quinone. 17DMAG demonstrated the greatest rate of redox cycling catalyzed by purified human cytochrome P450 reductase, whereas 17AAG again had the slowest rate.

Interaction of BA Hsp90 Inhibitors with Reduced Glutathione.

The interaction of BAs, including GM, 17DMAG, 17AAG, 17AG, and 17AEP-GA, with glutathione was measured by HPLC and further confirmed by LC-MS (FIGS. 4 and 5). Reaction conditions were: 50 µM BA and 5 mM GSH were incubated in 50 mM potassium phosphate buffer, pH 7.4 (1 ml) at room temperature in the absence and presence of 11.8 µg of rhNQO1 and 500 µM NADH. BA-GSH conjugate formation was analyzed by HPLC at 270 nm and further confirmed by LC-MS. The amount of BA glutathione conjugate formation was quantified using [3H] glutathione. In reactions in phosphate buffer at pH 7.4 and room temperature using 5 mM reduced glutathione and 50 µM BA, approximately 45 µM GMH2-SG conjugate was formed within 5 mM, which then slowly oxidized to GM-SG (FIG. 4, A). This indicates formation via a classic 1,4-reductive Michael addition generating the hydroquinone conjugate intermediates, which are then oxidized to quinone conjugates. Under the same conditions, approximately 47 µM 17DMAG-SG conjugate was formed within 4 h, whereas 17DMAGH2-SG was not detected (FIG. 5, A). This is likely because of the instability of 17DMAGH2-SG conjugate and its rapid oxidation to 17DMAG-SG during analysis. The identity of glutathione adducts was confirmed by LC-MS analysis (FIG. 4, D and FIG. 5, D). Conversely, the formation of 17AAG-SG and 17AG-SG was very slow under these conditions. Even after 24 h, less than 15% of 17AAG or 17AG was conjugated with glutathione. Under the same conditions, about 90% of 17AEP-GA was conjugated with glutathione within 10 h. The relative rate of glutathione conjugate formation in this series of BAs was GM>17DMAG>17AEP-GA>17AAG and 17AG. BA-glutathione conjugate formation was pH dependent, and glutathione conjugates were not formed when the pH was <5.0.

These data demonstrate that GM (the most hepatotoxic BA in the series) had a greater propensity to undergo redox cycling reactions catalyzed by hepatic one-electron reductases and displayed markedly greater reactivity with thiols when compared with the least hepatotoxic analog, 17AAG. Therefore, minimizing the propensity of BA derivatives to undergo one-electron reduction and glutathione conjugation while maximizing their two-electron reduction to stable Hsp90 inhibitory hydroquinones, which are properties of the 19-substituted geldanamycin derivatives of the present invention, is a useful strategy for optimizing the therapeutic index of BAs.

The foregoing description of the present invention has been presented for purposes of illustration and description. The description is not intended to limit the invention to the form disclosed herein. Variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound having the chemical structure:

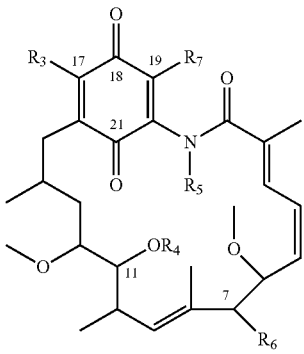

Formula I or a pharmaceutically-acceptable salt thereof;
wherein:
$R_3$ is $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is OH, $NH_2$, CN, $C_1$-$C_4$ alkyl, $C_1$-$C_6$ cycloalkyl, or alkylhalide.

2. The compound of claim 1, wherein:
$R_4$ and $R_5$ are H,
$R_6$ is $OC(=O)NH_2$, and,
$R_7$ is $CH_3$, or $CF_3$.

3. A compound having the chemical structure:

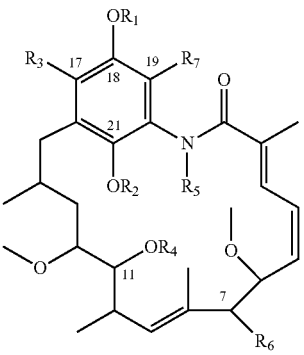

Formula II or a pharmaceutically-acceptable salt thereof;
wherein:
$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$, wherein X=an amino acid side chain;

$R_3$ is $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is OH, $NH_2$, CN, $C_1$-$C_4$ alkyl, $C_1$-$C_6$ cycloalkyl, or alkylhalide.

4. The compound of claim 3, wherein:

$R_4$ and $R_5$ are H, $R_6$ is $OC(=O)NH_2$, and, $R_7$ is $CH_3$, or $CF_3$.

5. A method of treating cancer in a mammal comprising administering a therapeutically-effective amount of a compound of claim 1 to the mammal.

6. The method of claim 5, wherein the compound is administered to the mammal in conjunction with an anti-cancer compound selected from the group consisting of a tyrosine kinase inhibitor, paclitaxel and doxorubicin.

7. The method of claim 5, wherein the compound is administered to the mammal in conjunction with medically supervised radiation therapy.

8. A pharmaceutical composition comprising at least one of the compounds of claim 1 and a metal chelating agent.

9. The pharmaceutical composition of claim 8 wherein the metal chelating agent is a copper chelating agent.

* * * * *